(12) United States Patent
Zubok et al.

(10) Patent No.: US 8,147,499 B2
(45) Date of Patent: Apr. 3, 2012

(54) DYNAMIC DISTRACTOR

(75) Inventors: Rafail Zubok, Midland Park, NJ (US); Zoya Royt, Fresh Meadows, NY (US)

(73) Assignee: SpineCore, Inc., Allendale, NJ (US)

( * ) Notice: Subject to any disclaimer, the term of this patent is extended or adjusted under 35 U.S.C. 154(b) by 1014 days.

(21) Appl. No.: 12/150,105

(22) Filed: Apr. 24, 2008

(65) Prior Publication Data

US 2009/0270870 A1   Oct. 29, 2009

(51) Int. Cl.
 *A61B 17/58* (2006.01)
(52) U.S. Cl. .................... 606/90; 606/57; 623/17.11
(58) Field of Classification Search ............... 606/90
 See application file for complete search history.

(56) References Cited

U.S. PATENT DOCUMENTS

| | | | |
|---|---|---|---|
| 1,425,845 A | 8/1922 | Foster | |
| 1,882,462 A | 10/1932 | Weber | |
| 2,546,287 A | 3/1951 | Zelgert | |
| 3,486,505 A | 12/1969 | Morrison | |
| 4,968,010 A | 11/1990 | Odobasic | |
| 5,015,247 A | 5/1991 | Michelson | |
| 5,122,130 A | 6/1992 | Keller et al. | |
| 5,306,309 A | 4/1994 | Wagner et al. | |
| 5,314,477 A | 5/1994 | Marnay et al. | |
| 5,571,109 A | 11/1996 | Bertagnoli et al. | |
| 5,667,347 A | 9/1997 | Matthews | |
| 5,683,399 A | 11/1997 | Jones | |
| 5,749,916 A | 5/1998 | Richelsoph | |
| 5,755,798 A | 5/1998 | Papavero et al. | |
| 5,766,252 A | 6/1998 | Henry et al. | |
| 6,159,211 A | 12/2000 | Boriani et al. | |
| 6,261,296 B1 | 7/2001 | Aebi et al. | |
| 6,478,800 B1 | 11/2002 | Fraser et al. | |
| 6,551,316 B1 | 4/2003 | Rinner et al. | |
| 6,582,451 B1 * | 6/2003 | Marucci et al. | 606/207 |
| 6,599,291 B1 * | 7/2003 | Foley et al. | 606/79 |
| 6,641,614 B1 | 11/2003 | Wagner et al. | |
| 6,652,233 B2 | 11/2003 | Otake et al. | |
| 6,712,825 B2 | 3/2004 | Aebi et al. | |
| 6,723,127 B2 | 4/2004 | Ralph et al. | |
| 6,733,532 B1 | 5/2004 | Gauchet et al. | |
| 6,755,841 B2 | 6/2004 | Fraser et al. | |
| 6,887,274 B2 | 5/2005 | Ralph et al. | |
| 6,989,032 B2 | 1/2006 | Errico et al. | |
| 7,008,432 B2 | 3/2006 | Schlapfer et al. | |
| 7,011,684 B2 | 3/2006 | Eckman | |
| 7,025,787 B2 | 4/2006 | Bryan et al. | |

(Continued)

FOREIGN PATENT DOCUMENTS

DE    20004812 U1    9/2000

(Continued)

OTHER PUBLICATIONS

International Search Report, PCT/US2009/002530, dated Jul. 10, 2009.

(Continued)

*Primary Examiner* — Thomas J Sweet
*Assistant Examiner* — Christopher D Prone
(74) *Attorney, Agent, or Firm* — Lerner, David, Littenberg, Krumholz & Mentlik, LLP

(57) ABSTRACT

A dynamic distractor is described for distracting an intervertebral space and determining a size of an artificial intervertebral disc to be implanted in the intervertebral space.

21 Claims, 14 Drawing Sheets

U.S. PATENT DOCUMENTS

| | | |
|---|---|---|
| 7,048,764 B2 | 5/2006 | Ferree |
| 7,060,099 B2 | 6/2006 | Carli et al. |
| 7,066,959 B2 | 6/2006 | Errico et al. |
| 7,070,598 B2 | 7/2006 | Lim et al. |
| 7,083,651 B2 | 8/2006 | Diaz et al. |
| 7,087,055 B2 | 8/2006 | Lim et al. |
| 7,118,580 B1 | 10/2006 | Beyersdorff et al. |
| 7,122,055 B2 | 10/2006 | Ralph et al. |
| 7,160,327 B2 | 1/2007 | Errico et al. |
| 7,169,182 B2 | 1/2007 | Errico et al. |
| 7,214,244 B2 | 5/2007 | Zubok et al. |
| 7,223,291 B2 | 5/2007 | Errico et al. |
| 7,235,081 B2 | 6/2007 | Errico et al. |
| 7,326,216 B2 | 2/2008 | Bertagnoli et al. |
| 7,491,241 B2 | 2/2009 | Errico et al. |
| 7,635,368 B2 | 12/2009 | Errico et al. |
| 7,713,302 B2 | 5/2010 | Ralph et al. |
| 2002/0111683 A1 | 8/2002 | Ralph et al. |
| 2002/0111684 A1 | 8/2002 | Ralph et al. |
| 2002/0116009 A1 | 8/2002 | Fraser et al. |
| 2002/0128714 A1 | 9/2002 | Manasas et al. |
| 2003/0009223 A1 | 1/2003 | Fehling et al. |
| 2003/0009224 A1 | 1/2003 | Kuras |
| 2003/0014111 A1 | 1/2003 | Ralph et al. |
| 2003/0040801 A1 | 2/2003 | Ralph et al. |
| 2003/0045939 A1 | 3/2003 | Casutt |
| 2003/0078662 A1 | 4/2003 | Ralph et al. |
| 2003/0078666 A1 | 4/2003 | Ralph et al. |
| 2003/0078667 A1 | 4/2003 | Manasas et al. |
| 2003/0083749 A1 | 5/2003 | Kuslich et al. |
| 2003/0100951 A1 | 5/2003 | Serhan et al. |
| 2003/0135278 A1 | 7/2003 | Eckman |
| 2003/0187453 A1 | 10/2003 | Schlapfer et al. |
| 2003/0187508 A1 | 10/2003 | Cauthen |
| 2003/0191533 A1 | 10/2003 | Dixon et al. |
| 2003/0191534 A1 | 10/2003 | Viart et al. |
| 2003/0195514 A1 | 10/2003 | Trieu et al. |
| 2003/0208271 A1 | 11/2003 | Kuras |
| 2003/0208273 A1 | 11/2003 | Eisermann et al. |
| 2003/0225416 A1 | 12/2003 | Bonvallet et al. |
| 2003/0229358 A1 | 12/2003 | Errico et al. |
| 2004/0002758 A1 | 1/2004 | Landry et al. |
| 2004/0030387 A1 | 2/2004 | Landry et al. |
| 2004/0106927 A1 | 6/2004 | Ruffner et al. |
| 2004/0204762 A1 | 10/2004 | Ralph et al. |
| 2004/0220582 A1 | 11/2004 | Keller |
| 2005/0119665 A1 | 6/2005 | Keller |
| 2005/0131542 A1 | 6/2005 | Benzel et al. |
| 2005/0177171 A1 | 8/2005 | Wetzler et al. |
| 2005/0182416 A1 | 8/2005 | Lim et al. |
| 2006/0074432 A1 | 4/2006 | Stad et al. |
| 2006/0241643 A1 | 10/2006 | Lim et al. |
| 2007/0016221 A1 | 1/2007 | Beyersdorff et al. |
| 2007/0123907 A1 | 5/2007 | Weber |
| 2007/0198092 A1 | 8/2007 | Errico et al. |
| 2007/0233143 A1 | 10/2007 | Josse et al. |
| 2007/0239162 A1 * | 10/2007 | Bhatnagar et al. ............... 606/69 |

FOREIGN PATENT DOCUMENTS

| | | |
|---|---|---|
| EP | 0369603 A1 | 5/1990 |
| EP | 1 222 903 A1 | 7/2002 |
| EP | 1946709 A1 | 7/2008 |
| WO | 9929271 A1 | 6/1999 |

OTHER PUBLICATIONS

Surgical Technique Using FRA Spacer Instruments, Technique Guide, Synthes Spine, 1998.

* cited by examiner

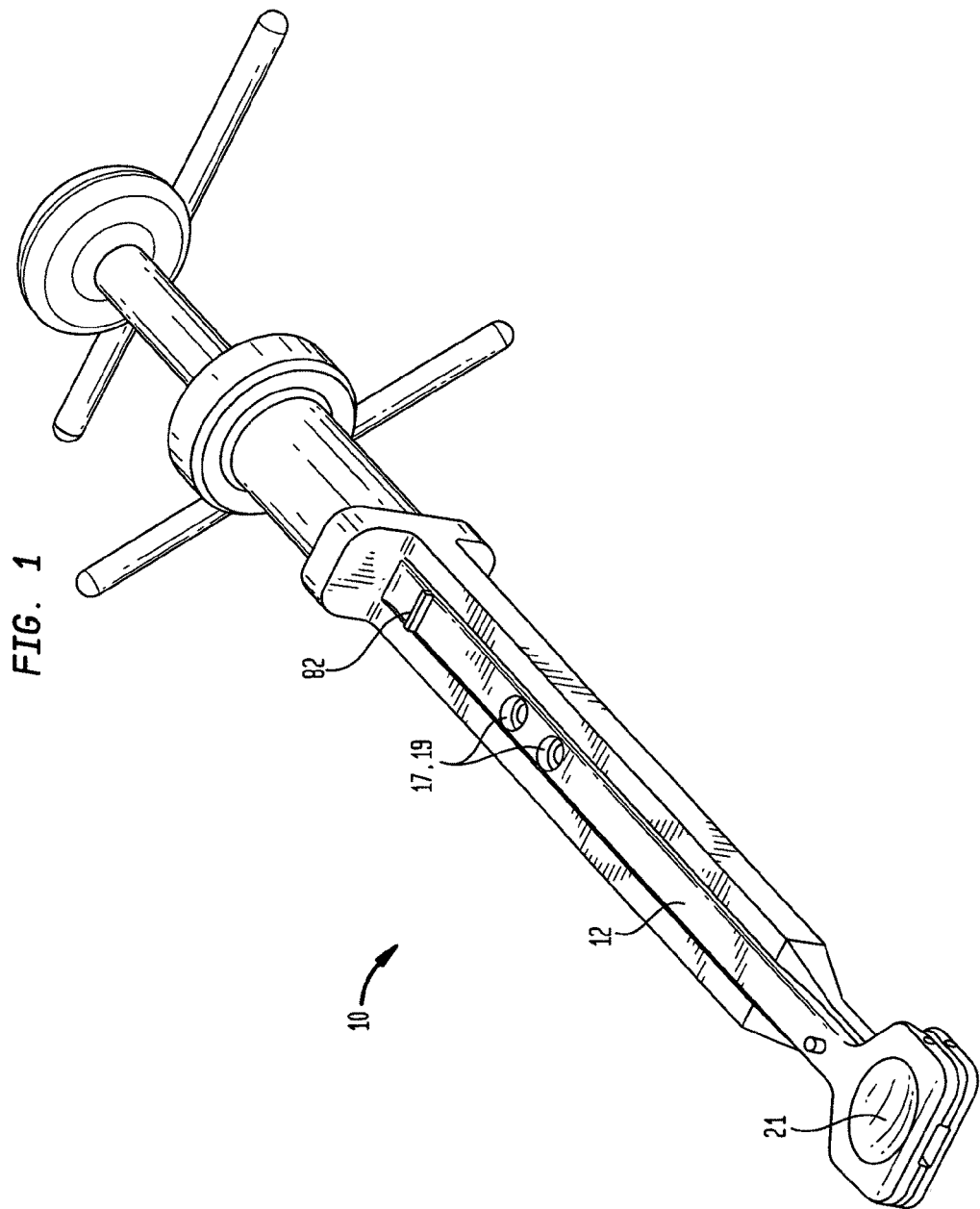

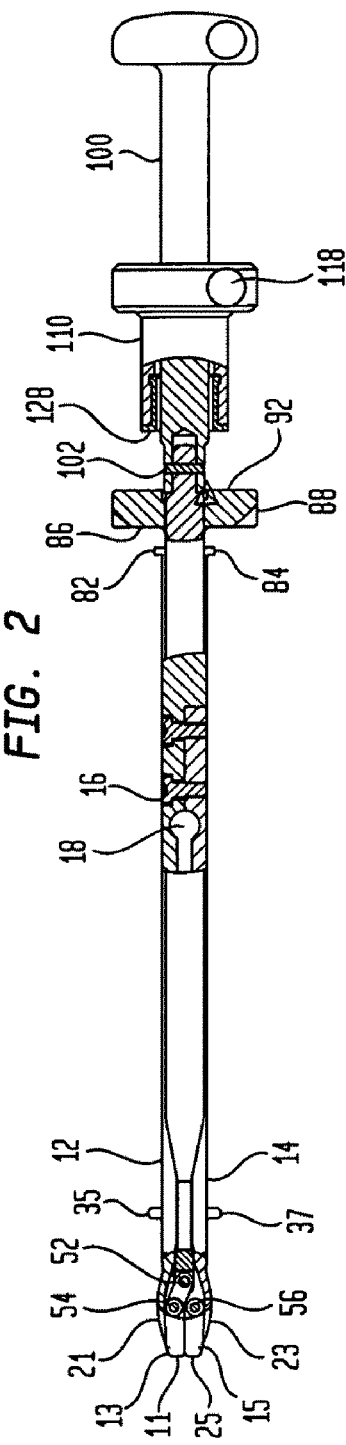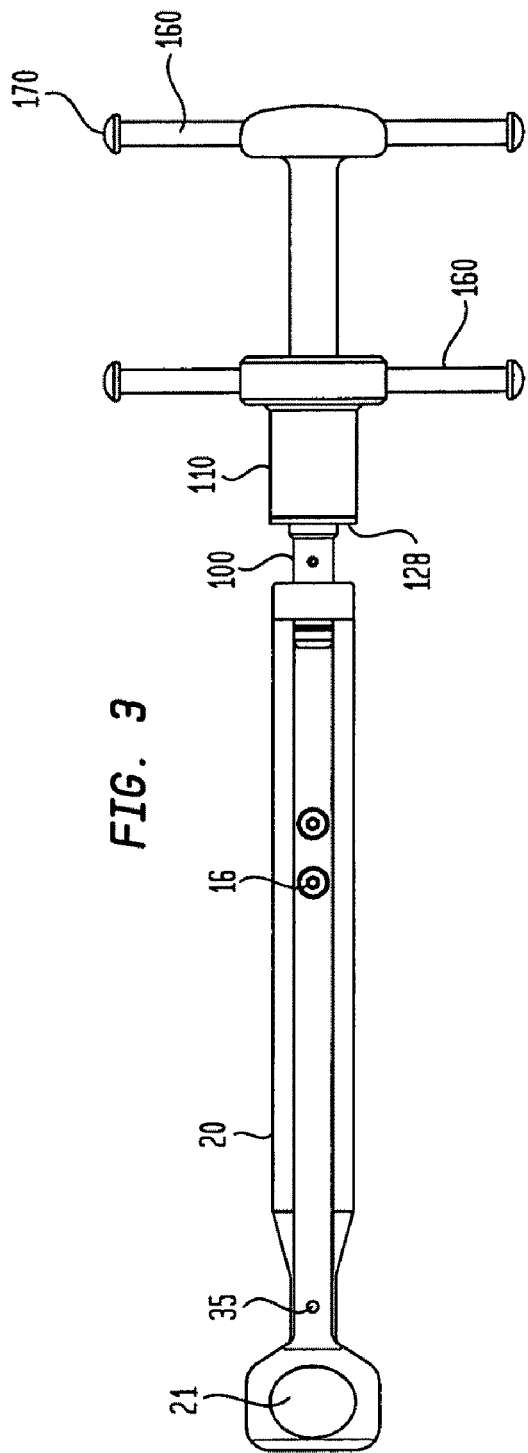

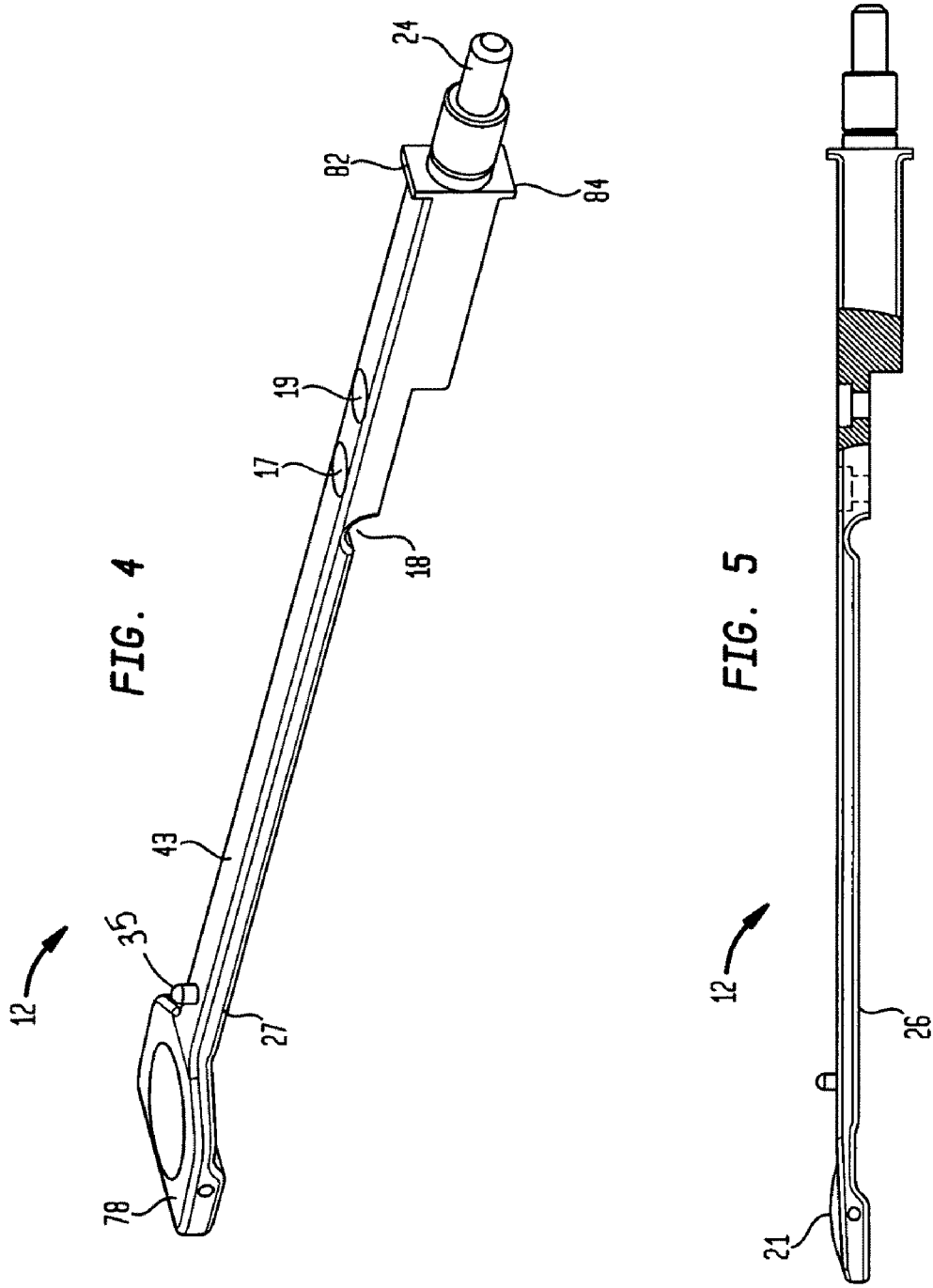

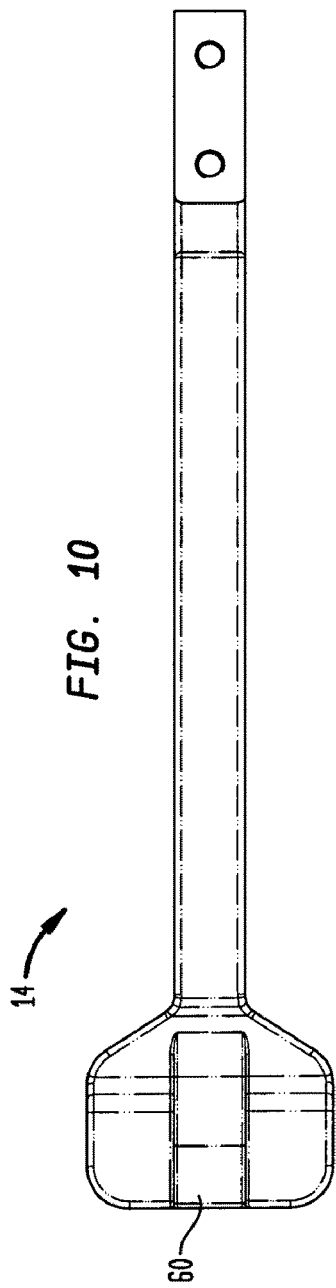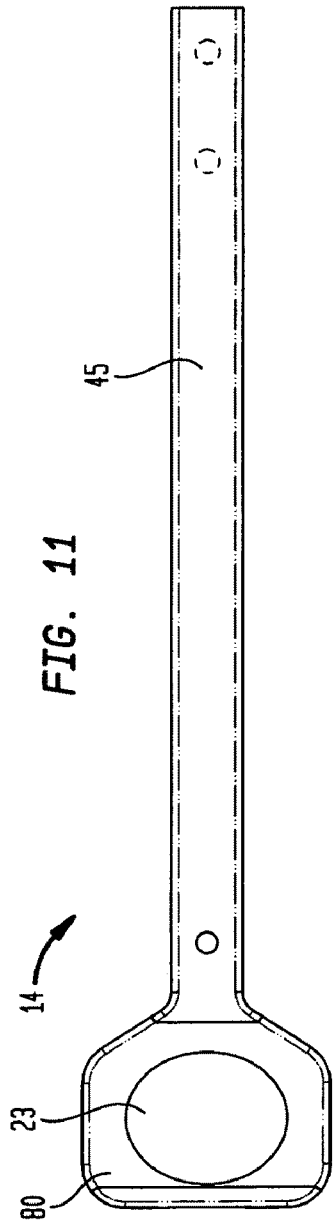

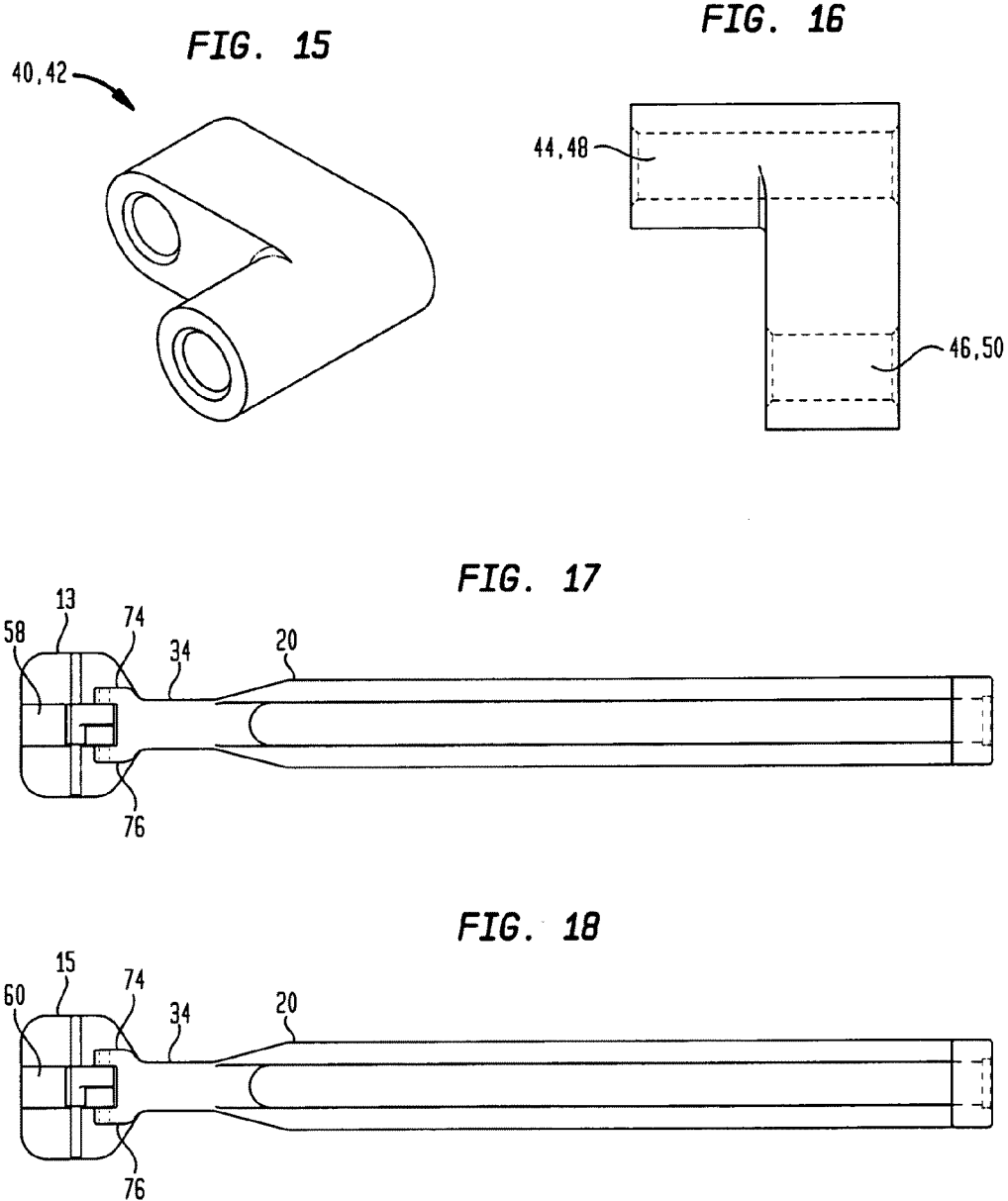

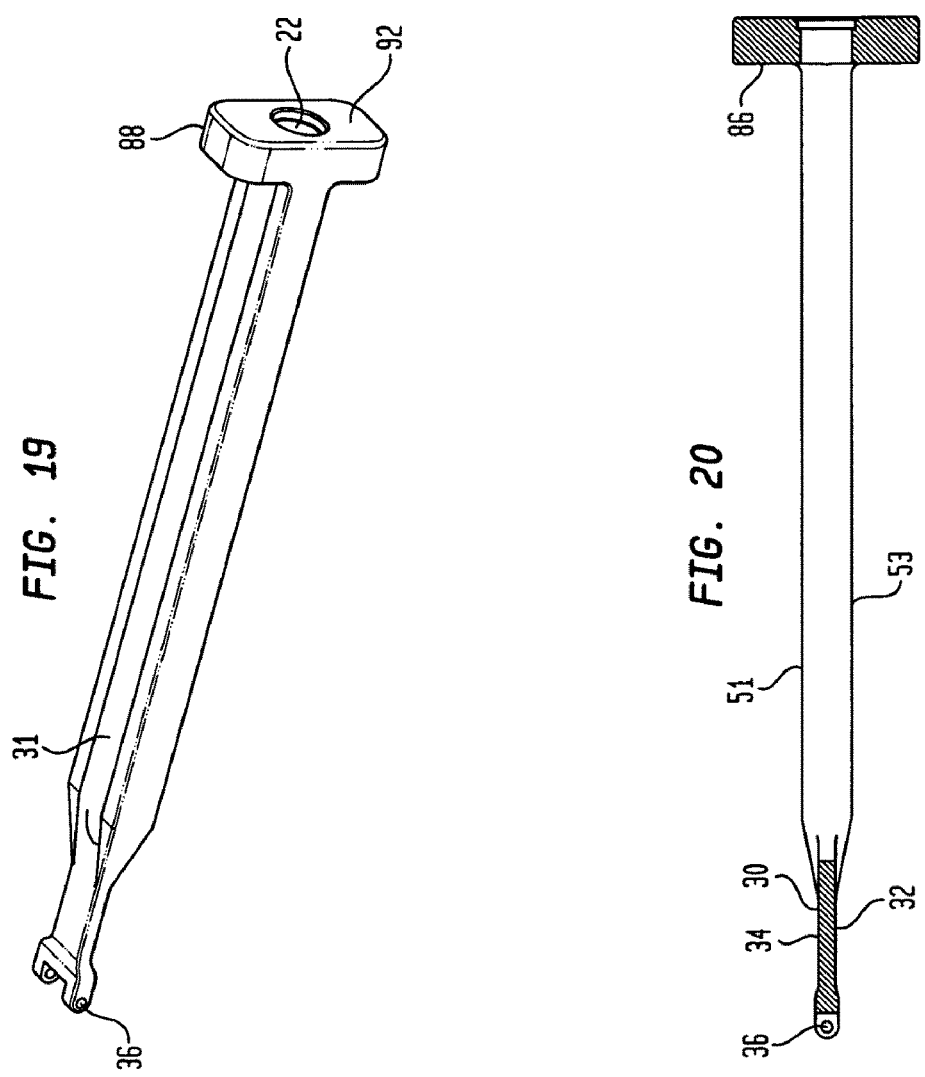

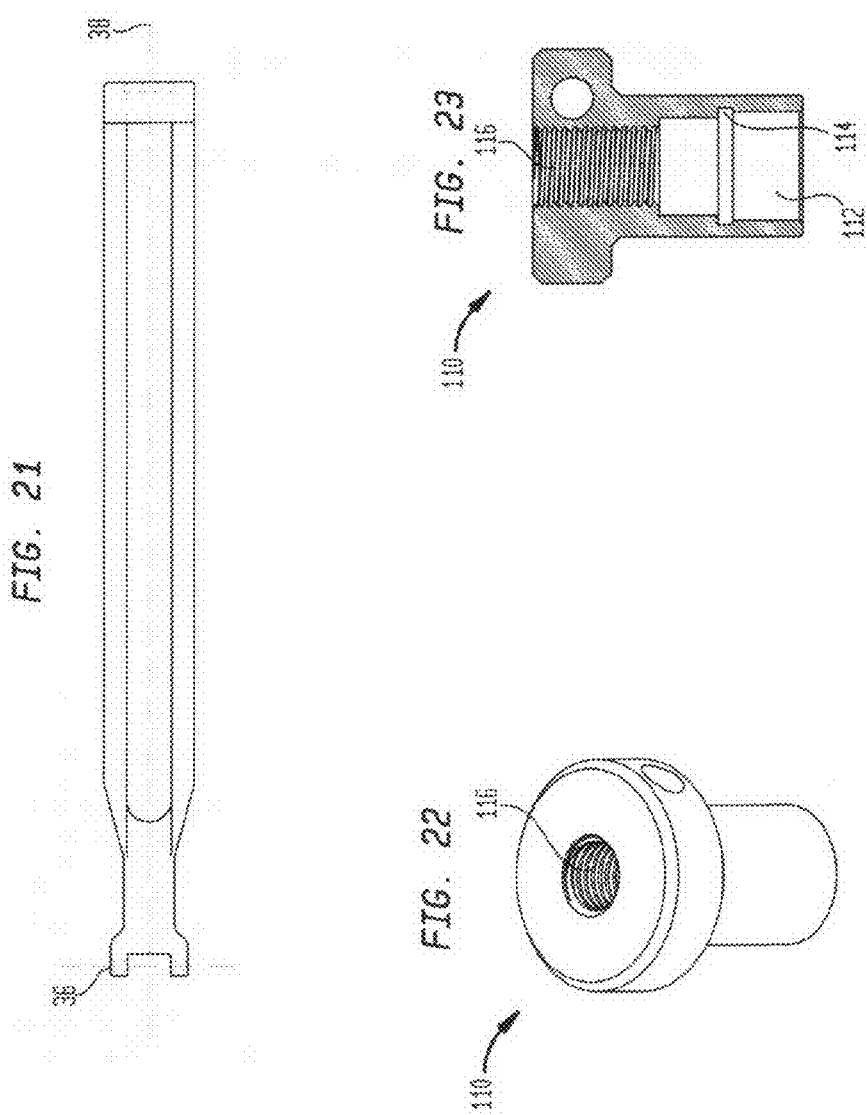

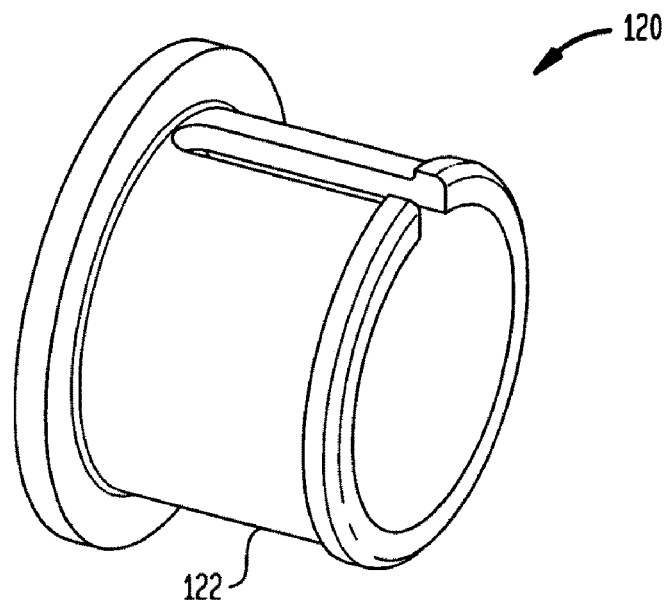
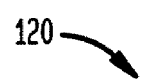

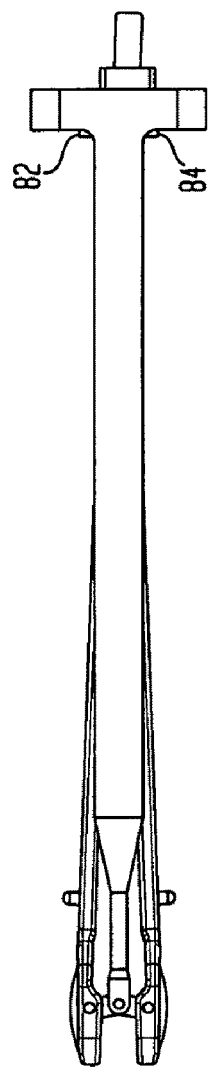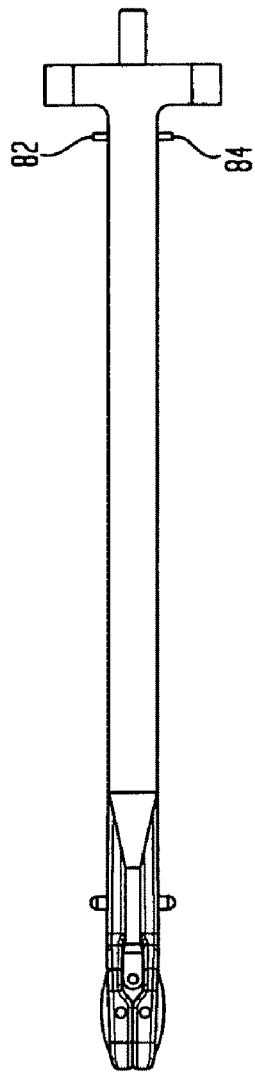

DYNAMIC DISTRACTOR

FIELD OF THE TECHNOLOGY

The present invention relates to a device for distracting an intervertebral space and determining the size of an artificial intervertebral disc to be implanted in the intervertebral space, and more particularly relates to a dynamic distractor having movable baseplates that may move toward and away from one another.

BACKGROUND OF THE INVENTION

The adult human spinal column is comprised of more than twenty discrete bones coupled sequentially to one another by a tri-joint complex that consists of an anterior vertebral body and the two postero-lateral facet joints, the vertebral bodies of adjacent bones being connected by spacers referred to as intervertebral discs. These more than twenty bones are anatomically categorized as being members of one of four classifications: cervical, thoracic, lumbar, or sacral.

The cervical portion of the spine, which comprises the top of the spine, up to the base of the skull, includes the first seven vertebrae. The intermediate twelve bones are the thoracic vertebrae, and connect to the lower spine comprising the five lumbar vertebrae. At the base of the spine are the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. With respect to the failure of the intervertebral disc, and the insertion of implants and/or height restorative devices, several methods and devices have been disclosed in the prior art that achieve immobilization and/or fusion of adjacent bones by implanting artificial assemblies in or on the spinal column.

More recently, the development of non-fusion implant devices, which purport to permit continued natural movement in the tri-joint complex, have provided great promise as a preferably alternative to fusion devices. The region of the back that needs to be corrected, as well as the individual variations in anatomy, determine the appropriate surgical protocol and implantation assembly. Generally, the preparation of the intervertebral space for the receipt of fusion or non-fusion devices involves removing the damaged disc material and thereafter distracting the adjacent vertebral bones to their appropriate distance apart. Once the proper height of the intervertebral space is restored, the fusion or non-fusion device can be implanted.

It is an object of the invention to provide instrumentation and methods that enable surgeons to more accurately, easily, and efficiently prepare the intervertebral space and implant fusion or non-fusion devices. Other objects of the invention not explicitly stated will be set forth and will be more clearly understood in conjunction with the descriptions of the preferred embodiments disclosed hereafter.

SUMMARY OF THE INVENTION

A first aspect of the present invention is a dynamic distractor. In accordance with one embodiment of the present invention, the dynamic distractor comprises an elongate pusher block movable in a proximal to distal direction along its longitudinal axis. The dynamic distractor further comprises a first elongate arm having a first baseplate ending at a distal end thereof and a second elongate arm having a second baseplate ending at a distal end thereof. Preferably, the first and second elongate arms are configured to lie adjacent to one another at proximal portions thereof and are configured to move toward and away from one another at distal portions thereof. Preferably, a first connector is rotatably coupled to the first baseplate, a second connector is rotatably coupled to the second baseplate, and the first connector and the second connector are also rotatably coupled to the distal portion of the pusher block.

In accordance with one embodiment of this first aspect of the present invention, the elongate pusher block includes a first aperture through the distal portion thereof, the first aperture having an axis perpendicular to the longitudinal axis of the pusher block.

In accordance with another embodiment of this first aspect of the present invention, the dynamic distractor further includes a pin located through the first aperture of the elongate pusher block such that the pin rotatably couples a second end of the first connector, a second end of the second connector, and the distal portion of the pusher block.

In accordance with yet another embodiment of this first aspect of the present invention, the first and second baseplates preferably each include a curvate groove cut into the bottom surface of the baseplates, the curvate groove adapted to receive a portion of the respective first and second connectors therein.

In accordance with still yet another embodiment of this first aspect of the present invention, each baseplate preferably includes an aperture therethrough, the aperture of the first and second baseplates each having an axis parallel to the axis of the axis of the first aperture of the pusher block.

In accordance with still yet another embodiment of this first aspect of the present invention, the dynamic distractor further includes a second and third pin, the second pin located through the aperture in the first baseplate such that the second pin rotatably couples a first end of the first connector with the first baseplate, the third pin located through the aperture in the second baseplate such that the third pin rotatably couples a first end of the second connector with the second baseplate.

Preferably, movement of the elongate pusher block in a distal direction with respect to the first and second elongate arms causes the arms to move away from one another in an inferior to superior direction. Preferably, movement of the elongate pusher block in a distal direction with respect to the first and second elongate arms causes the first connector to rotate in a clockwise manner and the second connector to rotate in a counter-clockwise manner thereby increasing the distance between the first and second baseplates.

In accordance with still yet another embodiment of this first aspect of the present invention, the pusher block preferably further includes a second aperture located through a distal portion thereof, the second aperture having an axis perpendicular to an axis of the first aperture of the pusher block.

In accordance with still yet another embodiment of this first aspect of the present invention, the pusher block preferably further includes a flange at the proximal end thereof, the flange extending outwardly in a perpendicular direction from the axis of the second aperture of the pusher block.

Preferably, at least one of the distal portions of the elongate arms is inserted through the second aperture of the pusher block such that a distal end of the elongate arm protrudes outwardly in a distal direction from the distal end of the flange. Preferably, the dynamic distractor further includes a handle attached to the proximal end of the first or second elongate arms such that the portion of the proximal end protruding from the flange is connected to the handle.

In accordance with still yet another embodiment of this first aspect of the present invention, the dynamic distractor preferably further includes a nut threadably connected to an outside surface of the handle. Preferably, rotation of the nut in a clockwise direction moves the nut in a distal direction with respect to the handle such that the distal end of the nut eventually engages the proximal end of the flange of the pusher block and causes the pusher block to also move in the distal direction.

In accordance with still yet another embodiment of this first aspect of the present invention, at least one of the first or second elongate arms preferably includes a stop portion extending outwardly from a top surface of the arms. Preferably, the stop portion of at least one of the first or second elongate arms inhibits movement of the pusher block in a distal direction with respect to the arms thereby inhibiting the further separation of the baseplates.

In accordance with still yet another embodiment of this first aspect of the present invention, the pusher block preferably further includes markings along its length on the top surface thereof between the distal end of the flange and the stop portion of at least one of the first or second elongate arms such that a user may measure the separation between the first and second baseplates by the position of the distal end of the flange with respect to the markings.

A second aspect of the present invention is a dynamic distractor. In accordance with one embodiment of this second aspect, the dynamic distractor comprises a distraction mechanism having a first arm and a second arm, the first arm including a first baseplate and the second arm including a second baseplate, the first and second arms pivotably coupled together. The dynamic distractor further comprises a pusher block having a distal portion located between the first and second arms of the distraction mechanism. Preferably, the dynamic distractor further comprises a linkage mechanism having a first linkage arm and a second linkage arm, the first linkage arm movably coupled to the first baseplate and movably coupled to the distal portion of the pusher block, the second linkage arm movably coupled to the second baseplate and movably coupled to the distal portion of the pusher block, wherein relative movement of the pusher block with respect to the distraction mechanism in a first direction expands the linkage mechanism causing the first and second baseplates to move away from one another.

In accordance with one embodiment of this second aspect of the present invention, relative movement of the pusher block with respect to the distraction mechanism in a second direction collapses the linking mechanism causing the first and second baseplates to move toward one another.

A third aspect of the present invention is a dynamic distractor. In accordance with one embodiment of this third aspect, the dynamic distractor comprises a linkage mechanism including a first linkage arm, a second linkage arm, and a pusher block, the first linkage arm having a first end pivotably coupled to a distal portion of the pusher block, the second linkage arm having a first end pivotably coupled to a distal portion of the pusher block. The dynamic distractor further comprises a distraction mechanism including a first elongate arm and a second elongate arm pivotably coupled together, the first elongate arm having a first baseplate rotatably coupled to a second end of the first linkage arm, the second elongate arm having a second baseplate rotatably coupled to a second end of the second linkage arm, wherein relative movement of the pusher block with respect to the distraction mechanism in a first direction expands the linkage mechanism causing the first and second baseplates to move away from one another.

In accordance with one embodiment of this third aspect of the present invention, relative movement of the pusher block with respect to the distraction mechanism in a second direction collapses the linking mechanism causing the first and second baseplates to move toward one another.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 1 is a perspective view of an assembled dynamic distractor of the present invention in a collapsed or closed position.

FIG. 2 is a side view in partial cross-section of the dynamic distractor of FIG. 1 showing the elements of the linkage mechanism and the relationship of the bushing and flange of the pusher block when the dynamic distractor is in the closed position.

FIG. 3 is a top view of the dynamic distractor of FIG. 1 showing the top surface of the first arm of the present invention.

FIG. 4 is a perspective view of the first arm of the dynamic distractor of FIG. 1.

FIG. 5 is a side view in partial cross-section of the first arm of the dynamic distractor as shown in FIG. 4.

FIG. 10 is a top view of the second arm of the dynamic distractor as shown in FIG. 8.

FIG. 11 is a bottom view of the second arm of the dynamic distractor as shown in FIG. 8.

FIG. 15 is a perspective view of a linkage arm of the dynamic distractor of the present invention.

FIG. 16 is a cross-section view of the linkage as shown in FIG. 15.

FIG. 17 is a bottom view of a linkage arm of the present invention connected to the pusher block and the first arm of the dynamic distractor of FIG. 1.

FIG. 18 is a top view of a linkage arm of the present invention connected to the pusher block and the second arm of the dynamic distractor of FIG. 1.

FIG. 19 is a perspective view of the pusher block of the dynamic distractor of the present invention.

FIG. 20 is a side view of a partial cross-section of the pusher block shown in FIG. 19.

FIG. 21 is a top view of the pusher block shown in FIG. 19.

FIG. 22 is a perspective view of a nut of the dynamic distractor of the present invention.

FIG. 23 is a side cross-section view of the nut shown in FIG. 22.

FIG. 24 is a perspective view of a bushing of the dynamic distractor of the present invention.

FIG. 25 is a side view of the bushing shown in FIG. 24.

FIG. 31 is a side view of the dynamic distractor of the present invention in an open position.

FIG. 32 is a side view of the dynamic distractor of the present invention in a closed position.

DETAILED DESCRIPTION

Figure 6:
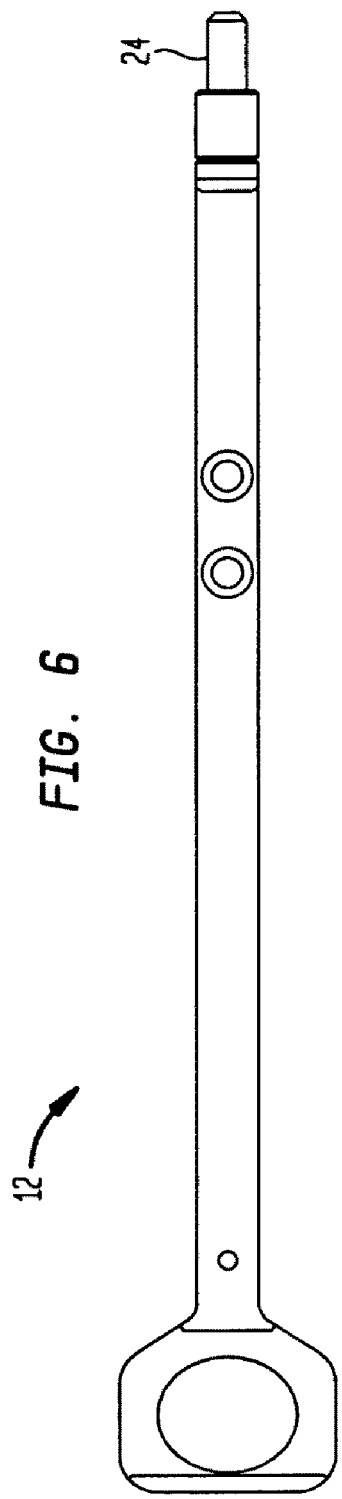
FIG. 6 is a top view of the first arm of the dynamic distractor as shown in FIG. 4.
Figure 7:
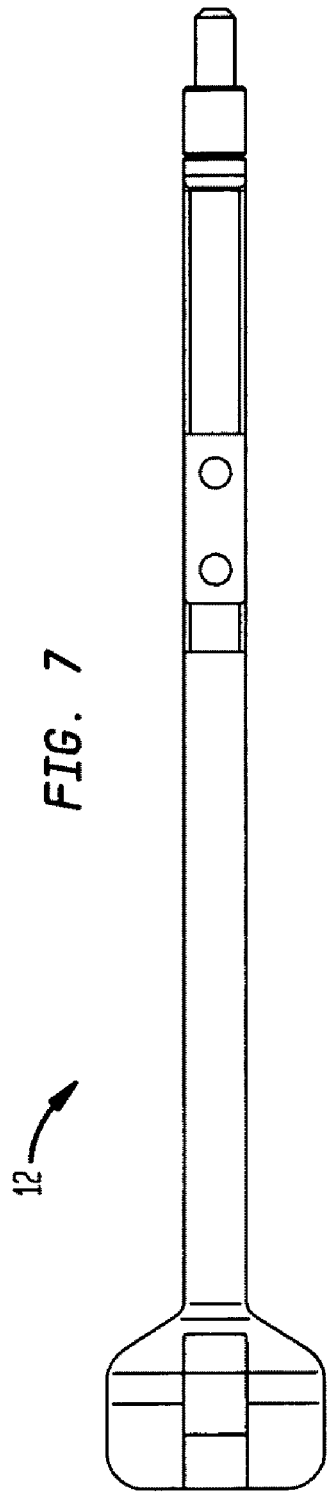
FIG. 7 is a bottom view of the first arm of the dynamic distractor as shown in FIG. 4.
Figure 8:
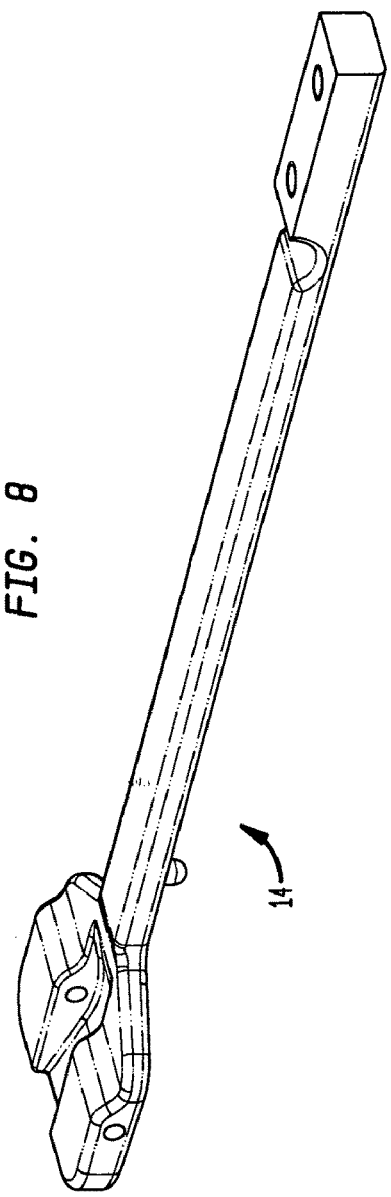
FIG. 8 is a perspective view of the second arm of the dynamic distractor of FIG. 1.
Figure 9:
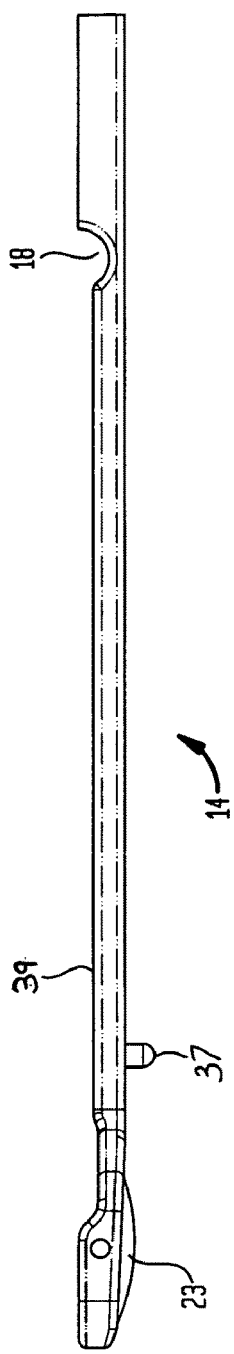
FIG. 9 is a side view of the second arm of the dynamic distractor as shown in FIG. 8.

As used herein, when referring to the dynamic distractor of the present invention, the term "distal end" means the end of the distractor which is furthest away from the user during use. As such, the term "proximal end" means the portion of the distractor which is closest to the user during use.

Referring to the drawings, wherein like reference numerals refer to like elements, there is shown in FIGS. 1-32 an embodiment of the dynamic distractor of the present invention designated generally by reference numeral 10.

Dynamic distractor 10 is provided primarily for distracting an intervertebral space according to the procedures described herein and/or for determining the appropriate size of an artificial intervertebral disc to be implanted (or whether a particular size can be implanted) into the distracted intervertebral space.

As shown in FIGS. 2-3, distractor 10 preferably includes a first elongate arm 12 and a second elongate arm 14. Preferably, first elongate arm 12 includes a first baseplate 13 ending at a distal end 11 thereof. Preferably, second elongate arm 14 includes a second baseplate 15 ending at a distal end 25 thereof. First and second baseplates 13, 15 are preferably integral with first and second elongate arms 12, 14 respectively. In alternative embodiments, first and/or second baseplates 13, 15 may be hinged with respect to first and second elongate arms 12, 14 respectively such that first and/or second baseplate 13, 15 may articulate with respect to first and second elongate arms 12, 14. Preferably, first and second baseplates 13, 15 are integral with first and second elongate arms 12, 14 respectively such that the adjacent vertebral bodies they are configured to distract remain substantially parallel to one another during distraction.

As shown in FIGS. 2 and 3, first and second elongate arms 12, 14 are shown assembled together via screws 16 plug welded in place. Screws 16 are shown passing through apertures 17, 19 of first and second elongate arms 12, 14. It should be understood that any means of fixing first elongate arm 12 and second elongate arm 14 at the location of apertures 17, 19 is within the scope of the present invention. For instance, first and second elongate arms 12, 14 may be screwed or welded together at the location of apertures 17, 19.

Located distal to screws 16 at approximately the middle of the lengths of the first and second elongate arms 12, 14 is formed a relief location 18. Preferably, relief location 18 is a middle point between first and second elongate arms 12, 14 wherein there is the most amount of space between arms 12, 14 as they lie in a closed position. When dynamic distractor 10 is in a closed position as shown in FIG. 2, first and second arms 12, 14 lie in a parallel orientation adjacent to one another along their lengths.

Preferably, first and second elongate arms 12, 14 are spring biased from approximately the location of relief location 18 to their proximal ends 11, 25 respectively. Preferably, this bias occurs by the formation of relief location 18 in combination with the strength of the material of which first and second elongate arms 12, 14 are made. The spring bias orients baseplates 13, 15 to a normally closed, minimum height configuration.

As dynamic distractor 10 moves into an open position as shown generally in FIGS. 31-32, first and second elongate arms 12, 14 begin to separate distally in a parabolic fashion from relief location 18 to their distal ends 11, 25 respectively. Preferably, first and second elongate arms 12, 14 separate from one another the greatest distance at distal ends 11, 25 of dynamic distractor 10.

As described above, dynamic distractor 10 of the present invention is preferably used to distract the disc space between adjacent vertebral bodies of the spine. Preferably, dynamic distractor 10 is configured to distract the disc space an additional 1.5 to 2 mm after a preliminary distraction has been performed to restore the natural height of the disc space. The additional height created through the use of dynamic distractor 10 minimizes the risk of damage to the upper and lower vertebral endplates of adjacent endplates from implant fixation features during insertion.

Preferably, baseplates 13, 15 include an exterior that is formed like the implanted device that it is meant to approximate. Accordingly, each baseplate 13, 15 preferably includes on its outwardly facing surface a convex dome 21, 23 that is shaped like the convex dome of the corresponding baseplate of the implanted device that dynamic distractor 10 approximates (e.g., the convex domes 184a-b of the baseplates 168a-b of the artificial intervertebral disc 160 of FIGS. 1g-n of U.S. application Ser. No. 10/282,356 incorporated herein by reference in its entirety). Preferably, baseplates 13, 15 proximal-to-distal and medial-to-lateral dimensions match or mimic the implanted device dimensions.

Preferably, each convex dome 21, 23 is smooth, rather than having a porous coating that is preferred for the convex domes 184a-b of the artificial intervertebral disc 160. Each baseplate 13, 15 does not include stabilizing spikes such as the stabilizing spikes 188a-b on the outwardly facing surfaces 186a-b of the artificial intervertebral disc 160. The omission of these device stabilizing and bone ingrowth encouraging structures and surfaces on dynamic distractor 10 enables the surgeon to test the size of the artificial intervertebral disc 160 to be implanted without damage to the prepared bone bed.

Preferably, baseplates 13, 15 of dynamic distractor 10 are inserted into an appropriate intervertebral disc space. First baseplate 13 should preferably lie adjacent to a bottom endplate of a vertebral body. Preferably, second baseplate 15 should lie preferably against a top endplate of an adjacent vertebral body. Depth stop pins 35 and 37 of the first and second elongate arms 12, 14 respectively are suitably located to abut the anterior surfaces of adjacent vertebral bodies such that the dynamic distractor 10 does not advance too far into an intervertebral disc space.

Generally, first elongate arm 12 may be considered the top arm and second elongate arm 14 is the bottom arm of dynamic distractor 10 during use. When using the terms "top" and "bottom" in the present invention, it should be understood that first elongate arm 12 is the top arm and second elongate arm 14 is the bottom arm when dynamic distractor 10 is in a preferred position. It should be understood that a user may hold dynamic distractor 10 in such a manner that first elongate arm 12 is the bottom arm and second elongate arm 14 is the top arm.

Figure 12:
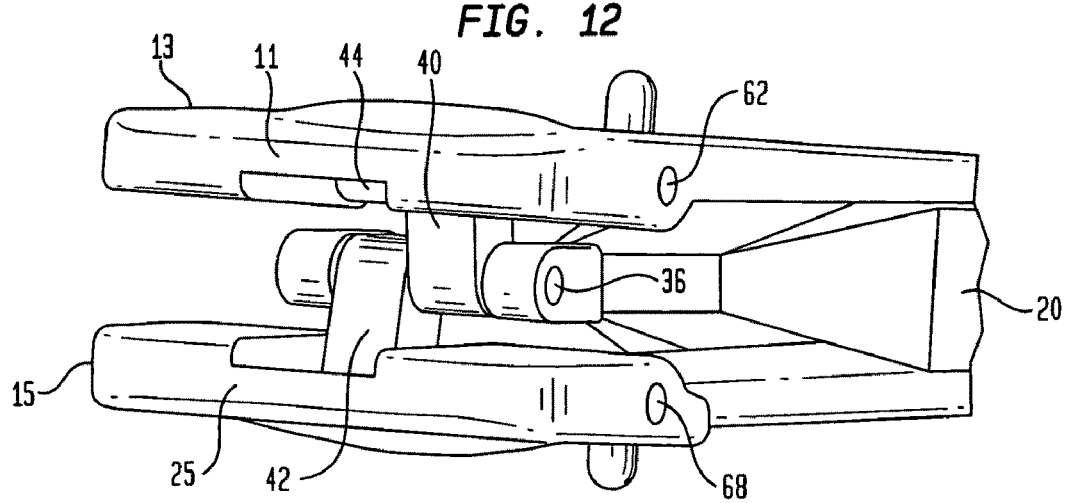
FIG. 12 is a perspective view of the distal end of the dynamic distractor of FIG. 1 in an expanded or open position showing the elements of the linkage mechanism with respect to the pusher block and first and second arms.

As further shown in at least FIGS. 3 and 12, a pusher block 20 lies between first and second elongate arms 12, 14 of dynamic distractor 10. Generally shown in FIGS. 19-21, pusher block 20 includes an aperture 22 at its proximal end. Aperture 22 is preferably configured to receive a proximal end portion 24 of first elongate arm 12. Preferably, to assemble first and second elongate arms 12, 14 and pusher block 20 together, proximal end portion 24 of first elongate arm 12 is first inserted into aperture 22 of pusher block 20 such that a bottom surface 26 of first elongate arm 12 is located adjacent to a top surface 30 of distal portion 34 of pusher block 20. Thereafter, second elongate arm 14 may be connected to first elongate arm 12 with screws 16 described above, such that a bottom surface 39 of second elongate arm 14 is located adjacent to a bottom surface 32 of distal portion 34 of pusher block 20.

When dynamic distractor 10 is first inserted into an intervertebral disc space it is in a closed or collapsed first position. In this collapsed first position, the top surface of first elongate arm 12 lies along substantially the same plane as the top surface of pusher block 20 and a top surface of second elongate arm 14 lies substantially along the same plane as bottom surface of pusher block 20.

When dynamic distractor 10 is in the closed position, an inner side surface 27 of first elongate arm 12 preferably rests against a top inner side surface 31 of pusher block 20 such that a top surface 43 of first elongate arm 12 lies substantially along the same plane of a top surface 51 of pusher block 20. Preferably, second elongate arm 14 is then assembled to first elongate arm 12 such that an inner side surface 29 of second elongate arm 14 rests against an inner bottom surface 33 of pusher block 20 such that a top surface 45 of second elongate arm 14 lies substantially along the same plane of a bottom surface 53 of the pusher block 20.

As shown in FIGS. 19-21, pusher block 20 preferably includes a distal portion 34 located between first and second baseplates 13, 15 when first and second elongate arms 12, 14 are assembled. Distal portion 34 of pusher block 20 preferably includes an aperture or bore 36 perpendicular to a longitudinal axis 38 of pusher block 20. Bore 36 is preferably configured to receive a cross-pin known in the art therein.

As shown in FIGS. 15-16, dynamic distractor 10 includes a first and second linkage arm 40, 42 configured to connect distal portion 34 of pusher block 20 to first and second baseplates 13, 15 respectively. As shown in FIGS. 2 and 17, first linkage arm 40 preferably includes a first hollow shaft portion 44 pivotably coupled to first baseplate 13 of first elongate arm 12 by a second cross-pin 54 and a second hollow shaft portion 46 pivotably coupled to distal portion 34 of pusher block 20 by a first cross-pin 52. As shown in FIGS. 2 and 18, second linkage arm 42 preferably includes a first hollow shaft portion 48 pivotably coupled to second baseplate 15 of second elongate arm 14 by a third cross-pin 56 and a second hollow shaft portion 50 pivotably coupled to distal portion 34 of pusher block 20 by first cross-pin 52.

Figure 13:
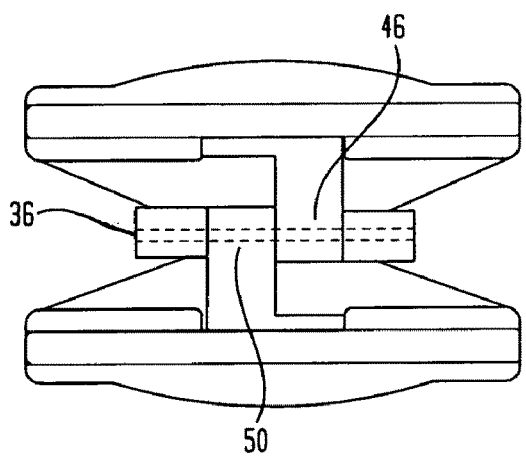
FIG. 13 is a front view of the dynamic distractor of FIG. 1 in an open position.
Figure 14:
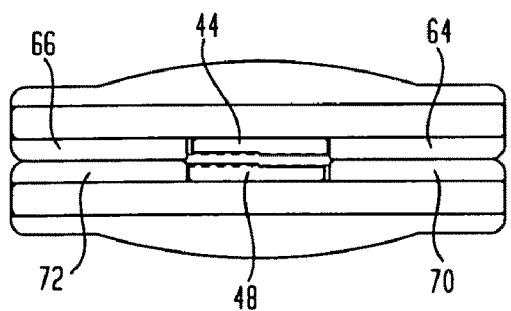
FIG. 14 is a front view of the dynamic distractor of FIG. 1 in a closed position.
Figure 26:
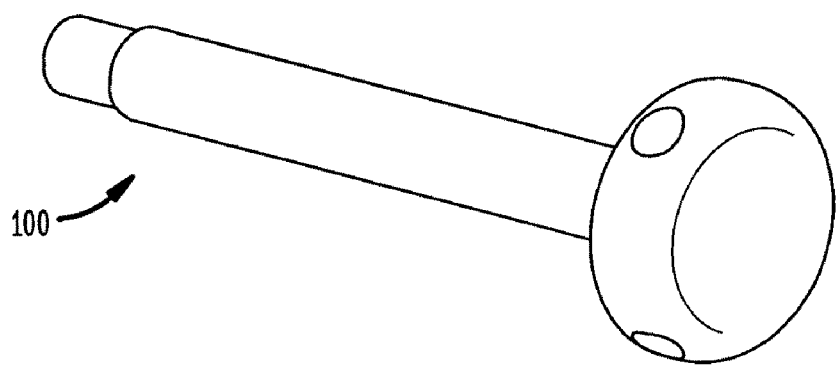
FIG. 26 is a perspective view of a handle body of the dynamic distractor of the present invention.
Figure 27:
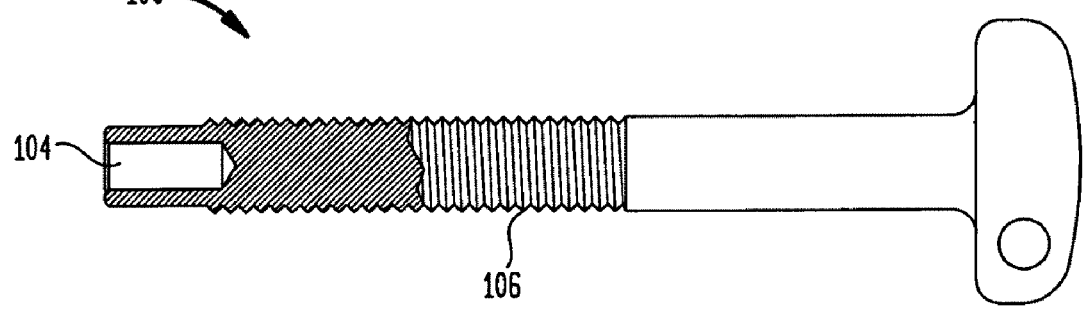
FIG. 27 is a side view of partial cross-section of the handle body shown in FIG. 26.

As shown in FIG. 12-14, first baseplate 13 preferably includes a bore 62 extending through its width from a first side portion 64 through a second side portion 66. Preferably, second cross-pin 54 is inserted into a bore 62 located in first side portion 64 of baseplate 13. As cross-pin 54 exits first side portion 64 it enters into first hollow shaft portion 44 of first linkage arm 40. As cross-pin 54 then exits first hollow portion 44 of first linkage arm 40 it enters into second side portion 66 of baseplate 13 such that first linkage arm 40 is pivotably connected to baseplate 13.

Second baseplate 15 preferably includes a bore 68 extending through its width from a first side portion 70 through a second side portion 72. Preferably, third cross-pin 56 is inserted into bore 68 located in first side portion 70 of baseplate 15. As cross-pin 56 exits first side portion 70 it enters into first hollow shaft portion 48 of second linkage arm 44. As cross-pin 56 then exits first hollow portion 48 of second linkage arm 44 it enters into second side portion 72 of baseplate 15 such that second linkage arm 44 is pivotably connected to baseplate 15.

As described above, distal portion 34 of pusher block 20 preferably includes a bore 36. Preferably, bore 36 extends through a first prong portion 74 and a second prong portion 76 of distal portion 34 of pusher block 20. Preferably, first cross-pin 52 is inserted into bore 36 located in first prong portion 74. As cross-pin 52 exits first prong portion 74 it preferably enters into second hollow shaft portion 46 of first linkage arm 40. As cross-pin 52 then exits second hollow shaft portion 46 it enters into second hollow shaft portion 50 of second linkage arm 42. As cross-pin 52 then exits second hollow shaft portion 50 it enters into second prong portion 76 of distal portion 34 of pusher block 20 such that first and second linkage arms 40, 42 are pivotably connected to proximal portion 34 of pusher block 20.

Preferably, first and second baseplates 13, 15 include a curved interior surface 58, 60 configured to accommodate first and second linkage arms 40, 42. Preferably, in the collapsed position, the distance between a top surface 78 of first baseplate 13 and a top surface 80 of second baseplate 15 is approximately 12 mm. Preferably, in a fully expanded position the distance between top surface 78 of first baseplate 13 and top surface 80 of second baseplate 15 are generally 20 mm apart.

The linkage mechanism of dynamic distractor 10 preferably includes distal portion 34 of pusher block 20 and first and second linkage arms 40, 42. The linkage mechanism is preferably configured such that first and second linkage arms 40, 42 cannot rotate into an over-center position. The center position is preferably referred to as wherein linkage arms 40, 42 would be perpendicular to longitudinal axis 38 of pusher block 20. Most distraction procedures in the spine will not require top surfaces 78, 80 of first and second baseplates 13, 15 to be greater than 20 mm apart, which is preferably the distance between top surfaces 78, 80 prior to the linkage arms 40, 42 reaching the center position.

Preferably, first and second elongate arms 12, 14 include a stop portion 82, 84 extending outwardly therefrom configured to prohibit a distal face 86 of a flange 88 of pusher block 20 from moving further in a distal direction. Stop portion 82, 84 of first and second elongate arms 12, 14 preferably prohibits first and second linkage arms 40, 42 from rotating into an over-center position as will be described further below.

As shown in FIGS. 2, 4, 26, and 27, a handle 100 is connected to proximal end portion 24 of first elongate arm 12 by a cross-pin 102. Handle 100 includes a recess 104 that is configured to receive at least a portion of proximal end portion 24. Preferably, proximal end portion 24 of first elongate arm 12 is press-fit into handle 100 such that proximal end portion 24 protrudes outwardly in a distal direction from flange 88 such that proximal end portion 24 may be received by recess 104 of handle 100. A cross-pin 102 acts to further secure proximal end portion 24 in recess 104.

Before handle 100 is assembled to proximal end portion 24 of first elongate arm 12, a nut 110 as shown in FIGS. 22-23, and a bushing 120 as shown in FIGS. 24-25, are assembled to handle 100. Preferably, nut 110 includes a recessed portion 112 configured to receive a first portion 122 of bushing 120 therein. First portion 122 of bushing is configured to snap-fit into recessed portion 112 of nut 110. A ridge 124 of bushing 120 preferably snaps into an inner recessed portion 114 of nut 110. After bushing 120 is secured within nut 110, an internal threaded portion 116 of nut 110 is threaded in a first clockwise direction onto a threaded portion 106 of handle 100. Preferably, nut 110 is completely threaded onto handle 100 before handle 100 is connected to distal end portion 24 of first elongate member 12.

An outer surface 128 of bushing 120 is configured to engage a proximal face 92 of flange 88 of pusher block 20. As nut 110 is rotated in a counterclockwise second direction along handle 100 of the dynamic distractor 10, outer surface 128 of bushing 120 eventually engages proximal face 92 of flange 88. Continued counterclockwise rotation of nut 110 in the second direction causes pusher block 20 to move in a distal direction causing the linkage mechanism of dynamic distractor 10 to expand such that dynamic distractor 10 moves from a closed position as shown in FIG. 31 to an expanded position as shown in FIG. 32.

In use, a user of dynamic distractor 10 of the present invention would hold handle 100 and would rotate nut 110 in a counterclockwise direction causing bushing 120 connected to nut 110 to move distally. In a first position, outer surface 128 of bushing 120 is located approximately 5-8 mm from proximal face 92 of flange 88 of pusher block 20. Accordingly, the internal threads 130 of bushing 120 must be rotated along the external threads 108 of handle 100 approximately 5-8 mm before outer surface 128 of bushing 120 reaches proximal face 92 of flange 88. As outer surface 128 of bushing 120 reaches proximal face 92 of flange 88, pusher block 20 is moved in a distal direction.

Preferably, in the collapsed position, the distance between a top surface 78 of first baseplate 13 and a bottom surface 80 of second baseplate 15 is approximately 10-12 mm. Dynamic distractor 10 is still in the collapsed position just as outer surface 128 of bushing 120 reaches proximal face 92 of flange 88 without moving pusher block 20 in the distal direction. At this point, any rotation of nut 110 in the counterclockwise direction will cause baseplates 13, 15 to separate and provide a distracting force to the disc space.

In one embodiment, a first 360° rotation of nut 110 in the clockwise direction may separate baseplates 13, 15 approximately 3-5 mm. A second 360° rotation of nut 110 in the clockwise direction may separate baseplates 13, 15 approximately another 1.5-2.5 mm. A third 360° rotation of nut 110 in the clockwise direction may separate baseplates 13, 15 approximately another 1-1.5 mm. A fourth 360° rotation of nut 110 in the clockwise direction may separate baseplates 13, 15 approximately another 0.25-1 mm. Preferably, when dynamic distractor 10 is in a fully open or expanded position the distance between top surface 78 of first baseplate 13 and bottom surface 80 of second baseplate 15 are approximately 18-20 mm apart.

It should be understood that nut 110 does not have to be rotated in 360° increments. Also it should be understood that baseplates 13, 15 will generally move toward one another the same distance they move away from one another if nut 110 is rotated back in the clockwise direction.

The amount of movement of the baseplates toward and away from one another may be determined by the pitch of the threads on handle 100 and nut 110. Also, the size of first and second linkage arms 40, 42 may determine the amount of movement of the baseplates toward and away from one another.

Preferably, movement of pusher block 20 in a distal direction causes first linkage arm 40 to rotate in a clockwise direction while causing second linkage arm 42 to rotate in a counterclockwise direction. This movement causes first and second baseplates 13, 15 to separate. As stated above, the movement of pusher block 20 in a distal direction will eventually be inhibited, if needed, by stop portions 82, 84 of first and second elongate arm 12, 14. Spring bias between first and second elongate arms 12, 14 naturally forces first and second elongate arms 12, 14 back into a collapsed position if a force is not maintained to keep pusher block 20 in a distal position. Preferably, the natural tendency of pusher block 20 is to move proximally in a direction back towards a neutral first position wherein first and second elongate arms 12, 14 may lie adjacent one another in a parallel orientation.

Preferably, markings 150 are preferably provided on top surface 51 of pusher block 20 and/or top surface 43 of first elongate arm 12 to quantify the separation of first and second baseplate 13, 15. A surgeon can read markings 150 on pusher block 20 and/or first elongate arm 12 to determine what size implant is suitable for the dimensioned intervertebral space. Preferably, markings 150 are located along the length of pusher block 20 between proximal end 86 of flange 88 and stop portion 82 of first elongate arm 12 such that a user may measure the separation between first and second baseplates 13, 15 by the position of the distal face 86 of flange 88 with respect to markings 150.

Figure 28:
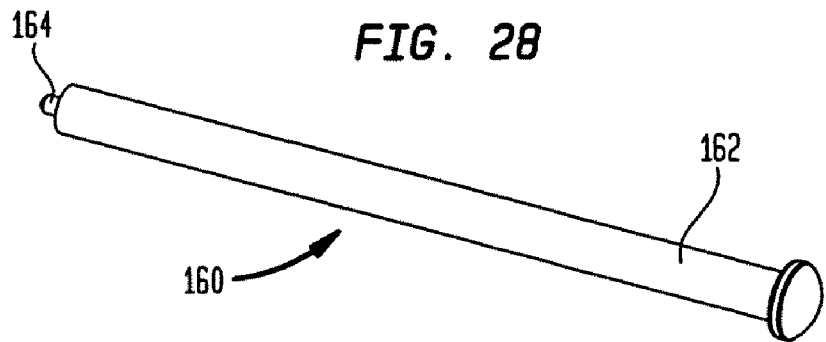
FIG. 28 is a perspective view of a handle lever of the dynamic distractor of the present invention
Figure 29:
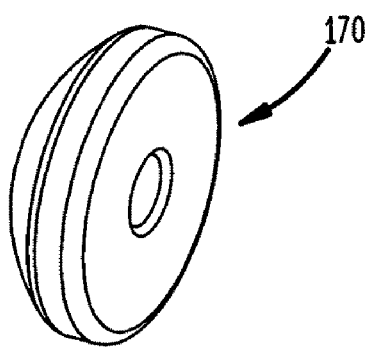
FIG. 29 is a perspective view of a cap for connecting to an open end of the handle lever of the dynamic distractor of the present invention.
Figure 30:
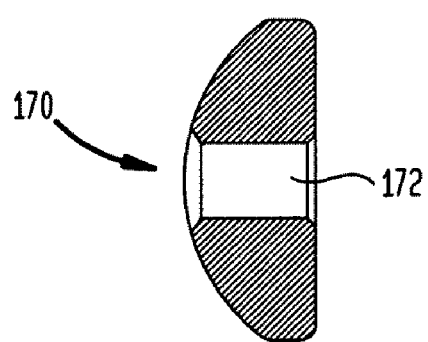
FIG. 30 is a side cross-section view of the cap shown in FIG. 29.

It should be understood that the force required to separate baseplates 13, 15 will increase as they separate, due to the compression of the spine. Therefore, to provide a mechanical advantage to the operator in the event that greater distraction is required, a lever 160 as shown in FIG. 28 may be used. An elongate shaft 162 of lever 160 may be inserted through an aperture 118 in nut 110 to provide the surgeon with additional leverage during rotation of nut 110. Lever 160 is preferably provided with a cap 170 shown in FIGS. 29-30 having a recess 172 therein. Preferably, cap 170 is press-fit or threaded to an open end 164 of lever 160 to secure lever 160 in aperture 118 of nut 110. Other quick-connect mechanisms known in the art may be used to connect cap 170 to lever 160. An additional lever 160 may be applied to handle 100 in the same manner as described with respect to nut 110. Preferably the levers 160 are permanently attached to the dynamic distractor 10. In this embodiment, levers 160 are inserted through the nut 110 and handle 100 and retained by caps 170. The levers 160 are slidably engaged with the nut 110 and handle 100 to allow multiple hand positions.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A dynamic distractor comprising:
an elongate pusher block having a distal portion movable in a proximal to distal direction along its longitudinal axis;
a first elongate arm having a first baseplate ending at a distal end thereof;
a second elongate arm having a second baseplate ending at a distal end thereof, wherein the first and second elongate arms each include a recess together which form a relief location between the first and second elongate arms, the first and second elongate arms being resiliently coupled and configured to lie adjacent to one another at proximal portions thereof and are configured to deflect away from one another such that the first and second elongate arms are curved from the relief location to the distal portions thereof when the first and second baseplates are separated from one another;
a first connector rotatably coupled to the first baseplate;
a second connector rotatably coupled to the second baseplate,
wherein the first connector and the second connector are also rotatably coupled to the distal portion of the pusher block.

2. The dynamic distractor of claim 1, wherein the elongate pusher block includes a first aperture through the distal portion thereof, the first aperture having an axis perpendicular to the longitudinal axis of the pusher block.

3. The dynamic distractor of claim 2, further including a pin located through the first aperture of the elongate pusher block such that the pin rotatably couples a second end of the first connector, a second end of the second connector, and the distal portion of the pusher block.

4. The dynamic distractor of claim 1, wherein the first and second baseplates each include a curvate groove cut into the interior surface of the baseplates, the curvate groove adapted to receive a portion of the respective first and second connectors therein.

5. The dynamic distractor of claim 4, wherein each baseplate includes an aperture therethrough, the aperture of the first and second baseplates each having an axis parallel to the axis of the axis of the first aperture of the pusher block.

6. The dynamic distractor of claim 5, further including a second and third pin, the second pin located through the aperture in the first baseplate such that the second pin rotatably couples a first end of the first connector with the first baseplate, the third pin located through the aperture in the second baseplate such that the third pin rotatably couples a first end of the second connector with the second baseplate.

7. The dynamic distractor of claim 1, wherein movement of the elongate pusher block in a distal direction with respect to the first and second elongate arms causes the arms to move away from one another in an inferior to superior direction.

8. The dynamic distractor of claim 1, wherein movement of the elongate pusher block in a distal direction with respect to the first and second elongate arms causes the first connector to rotate in a clockwise manner and the second connector to rotate in a counterclockwise manner thereby separating the distance between the first and second baseplates.

9. The dynamic distractor of claim 1, wherein the pusher block further includes a second aperture located through a proximal portion thereof, the second aperture having an axis perpendicular to an axis of the first aperture of the pusher block.

10. The dynamic distractor of claim 9, wherein the pusher block further includes a flange at the proximal end thereof, the flange extending outwardly in a perpendicular direction from the axis of the second aperture of the pusher block.

11. The dynamic distractor of claim 10, wherein at least one of the proximal portions of the elongate arms is inserted through the second aperture of the pusher block such that a proximal end of the elongate arm protrudes outwardly in a proximal direction from the proximal face of the flange.

12. The dynamic distractor of claim 11, wherein at least one of the first or second elongate arms includes a stop portion extending outwardly from a top surface of the arms.

13. The dynamic distractor of claim 12, wherein the stop portion of at least one of the first or second elongate arms inhibits movement of the pusher block in a distal direction with respect to the arms thereby inhibiting the further separation of the baseplates.

14. The dynamic distractor of claim 11, further including a handle attached to the proximal end of the first or second elongate arms such that the portion of the proximal end protruding from the proximal face of the flange is connected to the handle.

15. The dynamic distractor of claim 14, further including a nut threadably connected to an outside surface of the handle.

16. The dynamic distractor of claim 15, wherein rotation of the nut in a clockwise direction moves the nut in a distal direction with respect to the handle such that a distal end of the nut eventually engages the proximal face of the flange of the pusher block and causes the pusher block to also move in the distal direction.

17. The dynamic distractor of claim 16, wherein the pusher block further includes markings along its length on the top surface thereof between the distal face of the flange and the stop portion of at least one of the first or second elongate arms such that a user may measure the separation between the first and second baseplates by the position of the proximal end of the flange with respect to the markings.

18. A dynamic distractor comprising:
a distraction mechanism having a first arm and a second arm, the first arm including a first baseplate and the second arm including a second baseplate, the first and second arms are resiliently coupled together at proximal portions thereof and pivotably coupled together at distal portions thereof, the first and second arms each include a recess together which form a relief location between the first and second arms at the proximal portions thereof;
a pusher block having a distal portion located between the first and second arms of the distraction mechanism; and
a linkage mechanism having a first linkage arm and a second linkage arm, the first linkage arm movably coupled to the first baseplate and movably coupled to the distal portion of the pusher block, the second linkage arm movably coupled to the second baseplate and movably coupled to the distal portion of the pusher block,
wherein relative movement of the pusher block with respect to the distraction mechanism in a first direction expands the linkage mechanism causing the first and second baseplates to move away from one another with the first and second arms being curved from the relief location to the distal portions thereof.

19. The dynamic distractor of claim 18, wherein relative movement of the pusher block with respect to the distraction mechanism in a second direction collapses the linking mechanism causing the first and second baseplates to move toward one another.

20. A dynamic distractor comprising:
a linkage mechanism including a first linkage arm, a second linkage arm, and a pusher block, the first linkage arm having a first end pivotably coupled to a distal portion of the pusher block, the second linkage arm having a first end pivotably coupled to a distal portion of the pusher block; and
a distraction mechanism including a first elongate arm and a second elongate arm resiliently coupled together at proximal portions thereof and pivotably coupled together at distal portions thereof, the first and second elongate arms each include a recess together which form a relief location between the first and second arms at the proximal portions thereof, the first elongate arm having a first baseplate rotatably coupled to a second end of the first linkage arm, the second elongate arm having a second baseplate rotatably coupled to a second end of the second linkage arm,
wherein relative movement of the pusher block with respect to the distraction mechanism in a first direction expands the linkage mechanism causing the first and second baseplates to move away from one another with the first and second arms being curved from the relief location to the distal portions thereof.

21. The dynamic distractor of claim 20, wherein relative movement of the pusher block with respect to the distraction mechanism in a second direction collapses the linking mechanism causing the first and second baseplates to move toward one another.

* * * * *